(12) United States Patent
Butt et al.

(10) Patent No.: US 7,129,344 B1
(45) Date of Patent: Oct. 31, 2006

(54) NUCLEIC ACID ISOLATION

(75) Inventors: Neil James Butt, Cambridge (GB); Christopher Peter Jones, Hertfordshire (GB)

(73) Assignee: Whatman Bioscience Limited, Cambridge (GB)

( * ) Notice: Subject to any disclaimer, the term of this patent is extended or adjusted under 35 U.S.C. 154(b) by 0 days.

(21) Appl. No.: 09/856,336

(22) PCT Filed: Nov. 17, 1999

(86) PCT No.: PCT/GB99/03830

§ 371 (c)(1),
(2), (4) Date: Aug. 20, 2001

(87) PCT Pub. No.: WO00/29563

PCT Pub. Date: May 25, 2000

(30) Foreign Application Priority Data

Nov. 17, 1998 (GB) ................................ 9825215.8

(51) Int. Cl.
*C07H 21/02* (2006.01)
*C07H 21/04* (2006.01)
*C12N 15/00* (2006.01)
*C12N 15/10* (2006.01)
*C12N 1/06* (2006.01)
*C12Q 1/68* (2006.01)
*C12P 19/34* (2006.01)

(52) U.S. Cl. ............... 536/25.4; 536/25.41; 536/25.42; 435/320.1; 435/259; 435/6; 435/91.1

(58) Field of Classification Search .................. 435/64, 435/6, 69.1, 91.1, 91.3, 320.1; 514/565, 514/724; 536/25.4, 25.41, 25.42
See application file for complete search history.

(56) References Cited

U.S. PATENT DOCUMENTS

| 5,075,430 | A | 12/1991 | Little | |
|---|---|---|---|---|
| 5,637,687 | A | 6/1997 | Wiggins | 536/25.4 |
| 5,643,767 | A | 7/1997 | Fischetti et al. | 435/91.3 |
| 6,383,393 | B1 * | 5/2002 | Colpan et al. | 210/656 |

FOREIGN PATENT DOCUMENTS

| EP | 0 281 390 B1 | 9/1988 | |
|---|---|---|---|
| EP | 0 366 438 A1 | 5/1990 | |
| EP | 0 376 080 A1 | 7/1990 | |
| EP | 0 517 515 A3 | 12/1992 | |
| JP | 03101688 | * 4/1991 | .............. 435/64 |
| WO | WO 87/07645 | 12/1987 | |
| WO | WO 91/02089 | 2/1991 | |
| WO | WO 95/01359 | 1/1995 | |
| WO | WO 95/02049 | 1/1995 | |
| WO | WO 99/61603 | * 12/1999 | .............. 536/23.1 |

OTHER PUBLICATIONS

Sawadogo and Dyke, NAR, 1991, p. 19(3), p. 674.*
SCHP-445, Mutual Solubility of Liquids in a Binary Two-Phase System, Chemical Thermodynamics Lab, downloaded May 3, 2005.*
Nelson et al., Purification of Cloned and Genomic DNA by Guanidine Thiocyanate/Isobutyl Alcohol Fractionation, Analytical Biochemistry 207, 197-201 (1992).
Sambrook et al., Molecular Cloning, a Laboratory Manual, Second Edition, Cold Spring Harbor Laboratory Press, 1.22-1.24, 9.48, & E.12-E-14 (1989).
Voet et al., Biochemistry, Chapter 28, pp. 805-807, 815-816, & 844.
Old et al., Studies in Microbiology, vol. 2, Principles of Gene Manipulation, An Introduction to Genetic Engineering, Chapter 1 Section 1, pp. 7-10 & Chapter 3, Section 2, pp. 43-44.
Watson et al., Molecular Biology of the Gene, Fourth Edition, pp. 243-244.
Chomczynski, "A Reagent for the Single-Step Simulataneous Isolation of RNA, DNA and Proteins from Cell and Tissue Samples", BioTechniques, 15:3:532-536 (1993).
Chomszynski and Sacchi, "Single-Step Method of RNA Isolation by Acid Guanidinium Thlocyanate-Phenol-Chloroform Extraction" Analytical Biochemistry, 162:156-159 (1987).

* cited by examiner

*Primary Examiner*—Dave Trong Nguyen
*Assistant Examiner*—Maria Marvich
(74) *Attorney, Agent, or Firm*—David G. Conlin; Kathryn A. Piffat; Edwards Angell Palmer & Dodge, LLP

(57) ABSTRACT

A method for isolating plasmids DNA from a DNA containing material which comprises plasmid DNA and genomic DNA, comprising extracting the plasmid DNA into a water-immiscible organic solvent, a chaotrope and water under conditions to denature the genomic DNA and recovering the plasmid DNA from the organic phase.

47 Claims, No Drawings

NUCLEIC ACID ISOLATION

CROSS-REFERENCES TO RELATED APPLICATIONS

The present application is a 35 U.S.C. §371 national stage of PCT application PCT/GB99/03830, filed Nov. 17, 1999, which claims benefit of priority of United Kingdom Application 9825215.8 (filed Nov. 17, 1998), now United Kingdom Patent GB 2346615, the disclosures of which are incorporated herein by reference.

The present invention relates to a method for isolating nucleic acid, and particularly to a method for isolating plasmid DNA from a plasmid DNA-containing material.

Conventional procedures for the purification of nucleic acid, such as DNA, generally require multiple steps including lysis of source material followed by fractionation steps which may involve column chromatography. Where DNA manipulation is to be carried out, small scale DNA preparations are required routinely, often in large quantities for the purpose of screening DNA from the source cells. These processes are time consuming and labour intensive.

Various methods have been proposed in the purification of such DNA, including a precipitation method in EP-A-0376080, an ultrafiltration method in WO-A-87/07645 and EP-A-0517515 and cationic exchange resins in EP-A-0281390 and EP-A-0366438. A simplified method involving a filter, which is automatable, is disclosed in WO-A-95/02049.

Each of these methods suffers from a disadvantage that a series of steps is required and/or special apparatus is required to achieve sufficient purification of the plasmid DNA. A need therefore arises for a much simpler method involving readily-available apparatus and relatively inexpensive reagents. In a known approach for rapid purification of genomic DNA, RNA or protein, a mixture of phenol, chloroform and guanidine is used (Chomczynski, P. and Sacchi, N., 1987 Anal Biochem. 162: 156; Chomczynski, P., 1993 Biotechniques 15: 532) in which the DNA is extracted into an aqueous phase. This method is unsuitable for isolating plasmid DNA. Moreover, the use of phenol and chloroform is undesirable as these are toxic substances.

The present invention aims to overcome the disadvantages of the prior art and to provide a simplified method for isolating plasmid DNA.

Accordingly, the present invention provides a method for isolating plasmid DNA from DNA containing material which comprises plasmid DNA and genomic DNA, comprising:

(i) extracting the plasmid DNA into a water-immiscible organic solvent capable of supporting plasmid DNA, by mixing the material with the organic solvent, a chaotrope and water under conditions to denature the genomic DNA; optionally separating the organic and aqueous phases of step (i); and (ii) recovering the plasmid DNA from the organic phase.

Accordingly, the present invention provides a "one step" method which is simple to perform and which requires no specialised laboratory apparatus. It is surprisingly found that this method is capable of extracting plasmid DNA to high purity and with particularly low or zero contamination from genomic DNA which might be present in the plasmid DNA-containing material. In a preferred arrangement, the organic solvent is capable of selectively supporting the plasmid DNA with the exclusion of genomic DNA present in the plasmid DNA-containing material.

The method of the present invention may be performed on a small routine laboratory scale working with solution volumes of microlitres or milliliters. Alternatively, the method may be scaled up even to pilot or industrial scale involving volumes of liters or greater.

In extraction step (i), the DNA-containing material is mixed with the reagents under conditions to denature the genomic DNA typically whereby the plasmid DNA is partitioned into an organic phase and the genomic DNA is partitioned into an aqueous phase. Such conditions include basic conditions or elevated temperature. Suitable elevated temperatures are of at least 65° C. and more preferably in the range 70 to 95° C. for a time sufficient to denature the plasmid DNA such as from about 30 s to about 10 mins, preferably around five minutes. Incubation times longer than about 10 minutes at elevated temperature should not adversely affect the plasmid DNA but are undesirable for using the organic solvent. In a preferred arrangement, basic conditions are used in which a base is present. The base is typically a hydroxide such as an alkali metal hydroxide, preferably sodium hydroxide. The base is preferably present at a concentration in the range 100 mM to 200 mM. Incubation time is usually in the range from about 30 s to about 10 mins, preferably around five minutes. Excessive incubation under basic conditions can damage the plasmid DNA.

Without wishing to be bound by theory, it is thought that differential solubility between plasmid and genomic DNA under denaturing condition may result in plasmid DNA in an undenatured or reversibly denatured state partitioning into the organic phase. In contrast denatured genomic DNA partitions into the aqueous phase.

The organic solvent must be immiscible with the aqueous phase and preferably comprises an alcohol which may be aliphatic or aromatic and which may be linear or branched chain. The alcohol is preferably a $C_3$ to $C_6$ alcohol, more preferably a $C_4$ to $C_6$ alcohol and most preferably comprises a butanol such as N-butanol.

The chaotrope may be any normally-recognised chaotrope and is preferably selected from guanidine hydrochloride, guanidine thiocyanate, sodium perchlorate and mixtures thereof. A preferred chaotrope is guanidine hydrochloride. Typically, the chaotrope is present at a concentration in the range 0.7M to 1.2M, based on the combination of organic solvents, chaotrope water. The concentration of the chaotrope is preferably about 0.9M.

The amount of organic solvent is typically in the range from 20 to 70% based on the volume of the combination of organic solvent, chaotrope or water and is preferably in the range from 35 to 50%, more preferably around 42%.

The exact organic solvent, chaotrope, base and amounts thereof are readily determinable by routine experimentation. Each of these reagents may be mixed with the DNA-containing material in any order or may be premixed prior to addition to the plasmid-containing material. In a convenient arrangement, the organic solvent, chaotrope, base and water are combined to form an extraction mixture. In this arrangement, the extraction step (i) comprises mixing the extraction mixture with the DNA-containing material.

At laboratory scale, the step (ii) of separating the organic and aqueous phases may be conveniently carried out by allowing the phases to separate or encouraging separation on the basis of density by a short spin in a microcentrifuge. Typically, either the organic or aqueous phase is removed from the other prior to recovery step (iii). For example, the organic phase containing the plasmid DNA may be transferred from one container to another by pipette prior to recovery. On a larger scale, removal of one phase from the other could be performed by any conventional method including pumping or running off by gravity one of the two phases.

In one arrangement, recovery step (iii) includes precipitation of the plasmid DNA from the organic solvent. For example, the DNA-containing organic phase may be mixed with a precipitating agent that can precipitate the plasmid DNA from the organic solvent and the precipitated plasmid DNA is separated from the solvent. The precipitated plasmid DNA may also be washed in a washing step. The precipitating agent may comprise an alcohol such as ethanol and may further comprise an acetate salt such as sodium acetate.

The DNA-containing material may comprise any known DNA-containing material such as a bacterial culture which may be lysed or unlysed.

In a further aspect, the present invention provides an extraction mixture for selectively extracting plasmid DNA from a DNA-containing material, which extraction mixture comprises a water-immiscible organic solvent capable of supporting plasmid DNA, a chaotrope and water. The extraction mixture preferably further comprises a base.

The organic solvent, chaotrope, base and amounts thereof are typically those described above.

The present invention will now be described in further detail, by way of example only, with reference to the following Examples.

EXAMPLE 1

General procedure

Bacterial culture (*E coli* containing pBluescript; 0.5 ml) was spun down in an eppendorf tube using a microcentrifuge and the supernatant was discarded. The pellet was resuspended in TE buffer (tris[hydroxymethyl]aminomethane hydrochloride 10 mM, EDTA 1 mM; pH8.0; 200 µl) to form a resuspended pellet containing both genomic and plasmid DNA. An extraction mixture was selected according to the Table below, mixed very well and 0.5 ml thereof was added to the resuspended pellet and gently mixed. The eppendorf containing the mixture was spun in a microcentrifuge for 30 seconds to yield two phases; an upper organic phase and a lower aqueous phase. The organic phase was removed carefully to a fresh eppendorf tube avoiding any contaminating debris. Following measurement of the volume of the removed organic phase, sodium acetate (0.1 vols; 3M) and ethanol were added (2 vols) to precipitate the plasmid DNA. The eppendorf was spun in a microcentrifuge for 20 minutes and the ethanol supernatant removed. The pellet was rinsed with fresh ethanol (70%; 200 µl) and spun for 5 minutes. The ethanol was removed and the pellet dried and resuspended in water (20 µl). The resultant plasmid-containing DNA solution could then be assayed by visualisation on an agarose gel and the amount of DNA determined quantitatively by spectrophotometry or by fluorescence.

Table of Extraction Mixtures Tested

| CHAOTROPE | NaOH | SOLVENT | PLASMID DNA RECOVERY |
|---|---|---|---|
| GuSCN 0.9 M | 150 mM | N-Butanol 42% | Poor |
| GuSCN 0.9 M | 90 mM | N-Butanol 42% | Poor |
| GuSCN 0.9 M | 200 mM | N-Butanol 42% | Poor |
| GuSCN 0.9 M | 90 mM | N-Butanol 20% | Poor |
| GuSCN 0.9 M | 150 mM | N-Butanol 20% | Poor |
| GuSCN 0.9 M | 200 mM | N-Butanol 20% | Good |
| GuSCN 0.9 M | 90 mM | N-Butanol 70% | No |
| GuSCN 0.9 M | 150 mM | N-Butanol 70% | No |
| GuSCN 0.9 M | 200 mM | N-Butanol 70% | No |
| GuHCl 0.9 M | 90 mM | N-Butanol 42% | Good |
| GuHCl 0.9 M | 150 mM | N-Butanol 42% | Good |
| GuHCl 0.9 M | 200 mM | N-Butanol 42% | Good |
| GuHCl 0.9 M | 90 mM | N-Butanol 20% | OK |
| GuHCl 0.9 M | 150 mM | N-Butanol 20% | OK |
| GuHCl 0.9 M | 200 mM | N-Butanol 20% | Poor |
| GuHCl 0.9 M | 90 mM | N-Butanol 70% | OK |
| GuHCl 0.9 M | 150 mM | N-Butanol 70% | OK |
| GuHCl 0.9 M | 200 mM | N-Butanol 70% | Poor |
| GuHCl 0.9 M | 90 mM | 2 methyl propanol 20% | Poor |
| GuHCl 0.9 M | 150 mM | 2 methyl propanol 20% | Poor |
| GuHCl 0.9 M | 200 mM | 2 methyl propanol 20% | Poor |
| GuHCl 0.9 M | 90 mM | 2 methyl propanol 70% | No |
| GuHCl 0.9 M | 150 mM | 2 methyl propanol 70% | No |
| GuHCl 0.9 M | 200 mM | 2 methyl propanol 70% | No |
| GuHCl 0.9 M | 90 mM | 2 methyl propanol 42% | Poor |
| GuHCl 0.9 M | 150 mM | 2 methyl propanol 42% | OK |
| GuHCl 0.9 M | 200 mM | 2 methyl propanol 42% | OK |
| GuHCl 0.9 M | 90 mM | Butan-2-ol 42% | Poor |
| GuHCl 0.9 M | 150 mM | Butan-2-ol 42% | OK |
| GuHCl 0.9 M | 200 mM | Butan-2-ol 42% | Good |
| GuHCl 0.9 M | 90 mM | Butan-2-ol 20% | Poor |
| GuHCl 0.9 M | 150 mM | Butan-2-ol 20% | Poor |
| GuHCl 0.9 M | 200 mM | Butan-2-ol 20% | Poor |
| Na Perchlorate 0.9 M | 90 mM | N-Butanol 42% | Poor |
| Na Perchlorate 0.9 M | 150 mM | N-Butanol 42% | Poor |
| Na Perchlorate 0.9 M | 200 mM | N-Butanol 42% | Poor |
| Na Perchlorate 0.9 M | 90 mM | N-Butanol 70% | Poor |
| Na Perchlorate 0.9 M | 150 mM | N-Butanol 70% | Poor |
| Na Perchlorate 0.9 M | 200 mM | N-Butanol 70% | Poor |
| Na Perchlorate 0.9 M | 90 mM | N-Butanol 20% | Poor |
| Na Perchlorate 0.9 M | 150 mM | N-Butanol 20% | Poor |
| Na Perchlorate 0.9 M | 200 mM | N-Butanol 20% | Poor |
| Na Perchlorate 0.9 M | 200 mM | 2 methyl propanol 20% | OK |
| Na Perchlorate 0.9 M | 90 mM | 2 methyl propanol 70% | OK |
| Na Perchlorate 0.9 M | 150 mM | 2 methyl propanol 70% | Poor |
| Na Perchlorate 0.9 M | 200 mM | 2 methyl propanol 70% | Poor |
| Na Perchlorate 0.9 M | 90 mM | Butan-2-ol 42% | Poor |
| Na Perchlorate 0.9 M | 150 mM | Butan-2-ol 42% | Poor |
| Na Perchlorate 0.9 M | 200 mM | Butan-2-ol 42% | OK |
| Na Perchlorate 0.9 M | 90 mM | Butan-2-ol 20% | No |
| Na Perchlorate 0.9 M | 150 mM | Butan-2-ol 20% | No |
| Na Perchlorate 0.9 M | 200 mM | Butan-2-ol 20% | No |

Good Approximately 1 µg DNA recovery
OK Approximately 200 ng DNA recovery
Poor Just visible on agarose gel electrophoresis It may be concluded from these results that each recognised chaotrope works and that the guanidine hydrochloride is preferred over the guanidine thiocyanate which is, in turn, preferred over sodium perchlorate in terms of DNA recovery. As to solvents, butanol was found to work best whereas pentanol gave only poor DNA recovery. Ethanol and iso-propanol were found not to be water-immiscible. Of the butanols, N-butanol was found to be better than either butan-2-ol or 2 methyl propanol.

Whilst TE was used as the resuspension buffer in the procedure, water could also be used, as well as other resuspension buffers.

EXAMPLE 2

General Procedure for Extraction Using Heat Instead of Alkaline pH

Bacterial culture (*E coli* containing pBluescript; 0.5 ml) was spun down in an eppendorf tube using a microcentrifuge and the supernatant was discarded. The pellet was resuspended in TE buffer (tris[hydroxymethyl]aminomethane hydrochloride 10 mM, EDTA 1 mM; pH8.0; 200 μl) to form a resuspended pellet containing both genomic and plasmid DNA. An extraction mixture was selected according to the Table below, mixed very well and 0.5 ml was added to resuspended pellet and gently mixed. The eppendorf tube was then placed in a hot water bath at a temperature in the range 70 to 95° C. for five minutes and the contents frequently mixed. Care was taken with the lid of the eppendorf tube because of solvent expansion in the tube. The tube was then rapidly cooled on ice for three minutes, which had the effect of separating the plasmid and genomic DNA. The eppendorf containing the mixture was spun in a microcentrifuge for 30 seconds to yield two phases; an upper organic phase and a lower aqueous phase. The organic phase was removed carefully to a fresh eppendorf tube avoiding any contaminating debris. Following measurement of the volume of the removed organic phase, sodium acetate (0.1 vols; 3M) and ethanol were added (2 vols) to precipitate the plasmid DNA. The eppendorf was spun in a microcentrifuge for 20 minutes and the ethanol supernatant removed. The pellet was rinsed with fresh ethanol (70%; 200 μl) and spun for 5 minutes. The ethanol was removed and the pellet dried and resuspended in water (20 μl). The resultant plasmid-containing DNA solution could then be assayed by visualisation on an agarose gel and the amount of DNA determined quantitatively by spectrophotometry or fluorescence.

Results comparable to those of Example 1 were obtained although yields were slightly lower and minor contamination with genomic DNA was observed.

The invention claimed is:

1. A method for isolating plasmid DNA from genomic DNA in a DNA containing material which comprises plasmid DNA and genomic DNA, comprising the steps of:
   (i) extracting the plasmid DNA into butanol by mixing the material with butanol, a chaotrope, and water under conditions to denature the genomic DNA and forming an aqueous phase and a butanol phase,
      (a) wherein genomic DNA is in the aqueous phase and plasmid DNA is in the butanol phase; and
      (b) wherein the conditions to denature the genomic DNA comprise basic conditions or a temperature of at least 65° C.; and
   (ii) recovering the plasmid DNA from the butanol phase.

2. The method of claim 1, wherein the conditions to denature the genomic DNA comprise basic conditions in which a base is present.

3. The method of claim 2, wherein the base comprises a hydroxide.

4. The method of claim 3, wherein the hydroxide comprises sodium hydroxide.

5. The method of claim 2, wherein the butanol, the chaotrope, the base and the water are combined to form an extraction mixture, and extraction step (i) comprises mixing the extraction mixture with the plasmid DNA-containing material.

6. The method of claim 1, wherein the butanol is n-butanol, 2-methylpropanol, or butan-2-ol.

7. The method of claim 1, wherein the chaotrope is selected from the group consisting of guanidine hydrochloride, guanidine thiocyanate, sodium perchlorate, and mixtures thereof.

8. The method of claim 1, wherein the chaotrope comprises guanidine hydrochloride.

9. The method of claim 1, wherein the amount of butanol is in the range from 20 to 70% based on the volume of the combination of butanol, chaotrope and water.

10. The method of claim 9, wherein the amount of the butanol is in the range from 35 to 50%.

11. The method of claim 10, wherein the amount of the butanol is about 42%.

12. The method of claim 1, wherein the recovery step (ii) comprises mixing the butanol phase, which comprises plasmid DNA, with a precipitating agent that can precipitate the plasmid DNA from the butanol, and separating the precipitated plasmid DNA from the butanol.

13. The method of claim 12, wherein the recovery step (ii) further comprises a washing step in which the precipitated plasmid DNA is washed.

14. The method of claim 12 or claim 13, wherein the precipitating agent comprises an alcohol.

15. The method of claim 14, wherein the alcohol is ethanol.

16. The method of claim 12, wherein the precipitating agent further comprises an acetate salt.

17. The method of claim 16, wherein the acetate salt comprises sodium acetate.

18. The method of claim 1, which further comprises a step of separating the butanol and aqueous phases of step (i) prior to recovering the plasmid DNA.

19. The method of claim 18, wherein the step of separating the butanol and aqueous phases further comprises centrifugation of the mixture formed in step (i) to facilitate separation of the mixture into the butanol and aqueous phases.

20. The method of claim 1, wherein the DNA-containing material comprises a lysed or unlysed bacterial culture.

21. The method of claim 1, wherein the butanol, the chaotrope, and the water are combined to form an extraction mixture, and extraction step (i) comprises mixing the extraction mixture with the plasmid DNA-containing material.

22. The method of claim 1, wherein the chaotrope is present at a concentration of from 0.7M to 1.2M based on the combination of butanol, chaotrope and water.

23. The method of claim 22, wherein the concentration of the chaotrope is about 0.9M.

24. The method of claim 1, wherein genomic DNA is in the aqueous phase and plasmid DNA is in the butanol phase.

25. A method for isolating plasmid DNA from a DNA containing material which comprises plasmid DNA and genomic DNA, comprising the steps of:
   i extracting the plasmid DNA into butanol by mixing the material with butanol, a chaotrope, and water under conditions to denature the genomic DNA, a. wherein the chaotrope is present at a concentration of from 0.7M to 1.2M based on the combination of butanol, chaotrope and water; and b. wherein the conditions to denature the genomic DNA comprise basic conditions or a temperature of at least 65° C.; and ii. recovering the plasmid DNA from the butanol.

26. A method for isolating plasmid DNA from a DNA containing material which comprises plasmid DNA and genomic DNA, comprising the steps of:

i extracting the plasmid DNA into butanol by mixing the material with butanol, a chaotrope, and water under conditions to denature the genomic DNA, a. wherein the concentration of the chaotrope is about 0.9M; and b. wherein the conditions to denature the genomic DNA comprise basic conditions or a temperature of at least 65° C.; and ii. recovering the plasmid DNA from the butanol.

27. An biphasic extraction mixture for selectively extracting plasmid DNA from genomic DNA in a DNA-containing material which comprises plasmid DNA and genomic DNA, in an extraction process, wherein the extraction mixture comprises butanol, a chaotrope, and water, wherein the butanol in the extraction mixture forms an organic phase, which comprises plasmid DNA, during the extraction process.

28. The extraction mixture of claim 27, wherein the butanol is n-butanol, 2-methylpropanol, or butan-2-ol.

29. The extraction mixture of claim 27, wherein the butanol constitutes from 20 to 70% based on the volume of the extraction mixture.

30. The extraction mixture of claim 22, wherein the butanol constitutes from 35 to 50% of the extraction mixture.

31. The extraction mixture of claim 30, wherein the butanol constitutes about 42% of the extraction mixture.

32. The extraction mixture of claim 27, wherein the chaotrope is selected from the group consisting of guanidine hydrochloride, guanidine thiocyanate, sodium perchlorate, and mixtures thereof.

33. The extraction mixture of claim 32, wherein the chaotrope comprises guanidine hydrochloride.

34. The extraction mixture of claim 27, which further comprises a base.

35. The extraction mixture of claim 34, wherein the base comprises a hydroxide.

36. The extraction mixture of claim 35, wherein the hydroxide comprises sodium hydroxide.

37. An biphasic extraction mixture for selectively extracting plasmid DNA from genomic DNA in a DNA-containing material which comprises plasmid DNA and genomic DNA, in an extraction process, wherein the extraction mixture comprises butanol, a chaotrope, water, and a base, wherein the butanol in the extraction mixture forms an organic phase, which comprises plasmid DNA, during the extraction process.

38. The extraction mixture of claim 37, wherein the base comprises a hydroxide.

39. The extraction mixture of claim 38, wherein the hydroxide comprises sodium hydroxide.

40. An biphasic extraction mixture for selectively extracting plasmid DNA from a DNA-containing material which comprises plasmid DNA and genomic DNA, in an extraction process, wherein the extraction mixture comprises butanol, a chaotrope, and water, wherein the butanol constitutes from 35 to 50% of the extraction mixture and wherein the butanol in the extraction mixture forms an organic phase which comprises plasmid DNA, during the extraction process.

41. An biphasic extraction mixture for selectively extracting plasmid DNA from a DNA-containing material which comprises plasmid DNA and genomic DNA, in an extraction process, wherein the extraction mixture comprises butanol, a chaotrope, and water, wherein the butanol constitutes about 42% of the extraction mixture and wherein the butanol in the extraction mixture forms an organic phase, which comprises plasmid DNA, during the extraction process.

42. An extraction mixture for selectively extracting plasmid DNA from a DNA-containing material which comprises plasmid DNA and genomic DNA, which extraction mixture comprises butanol, a chaotrope, and water, wherein the concentration of chaotrope in the extraction mixture is from 0.7M to 1.2M.

43. An extraction mixture for selectively extracting plasmid DNA from a DNA-containing material which comprises plasmid DNA and genomic DNA, which extraction mixture comprises butanol, a chaotrope, and water, wherein the concentration of the chaotrope in the extraction mixture is about 0.9M.

44. A method for isolating plasmid DNA from genomic DNA in a DNA containing material which comprises plasmid DNA and genomic DNA, comprising the steps of:

i. extracting the plasmid DNA into butanol by mixing the material with butanol, a chaotrope, and water under conditions to denature the genomic DNA and forming an aqueous phase and a butanol phase, wherein genomic DNA is in the aqueous phase and plasmid DNA is in the butanol phase; and ii. recovering the plasmid DNA from the butanol phase.

45. The method of claim 44, wherein genomic DNA is in the aqueous phase and plasmid DNA is in the butanol phase.

46. An extraction mixture for selectively extracting plasmid DNA from genomic DNA in a DNA-containing material which comprises plasmid DNA and genomic DNA, in an extraction process, wherein the extraction mixture comprises butanol, a chaotrope, and water, wherein the butanol in the extraction solution forms an organic phase during the extraction process, wherein the concentration of chaotrope in the extraction mixture is from 0.7M to 1.2M.

47. The extraction mixture of claim 46, wherein the concentration of the chaotrope in the extraction mixture is about 0.9M.

* * * * *